United States Patent [19]

Reiffenrath et al.

[11] Patent Number: 5,209,866
[45] Date of Patent: * May 11, 1993

[54] HETEROCYCLIC 1,2-DIFLUOROBENZENE DERIVATIVES

[75] Inventors: Volker Reiffenrath, Rossdorf; Joachim Krause, Dieburg; Andreas Wächtler, Griesheim; Thomas Geelhaar, Mainz, all of Fed. Rep. of Germany

[73] Assignee: Merck Patent Gesellschaft mit beschrankter Haftung, Darmstadt, Fed. Rep. of Germany

[*] Notice: The portion of the term of this patent subsequent to Mar. 30, 2010 has been disclaimed.

[21] Appl. No.: 363,904

[22] Filed: May 15, 1989

[30] Foreign Application Priority Data

Mar. 10, 1988 [DE] Fed. Rep. of Germany ....... 3807871

[51] Int. Cl.$^5$ .................. C09K 19/34; C09K 19/12; C07D 211/70
[52] U.S. Cl. .................. 252/299.61; 546/339; 548/136
[58] Field of Search ............ 252/299.66, 299.61, 252/299.63; 548/136; 546/339

[56] References Cited

U.S. PATENT DOCUMENTS

| | | | |
|---|---|---|---|
| 4,368,135 | 1/1983 | Osman | 252/299.63 |
| 4,415,470 | 11/1983 | Eidenschink et al. | 252/299.63 |
| 4,514,317 | 4/1985 | Tuong et al. | 252/299.62 |
| 4,545,922 | 10/1985 | Eidenschink et al. | 252/299.63 |
| 4,551,264 | 11/1985 | Eidenschink et al. | 252/299.62 |
| 4,602,851 | 7/1986 | Jenner et al. | 350/350 R |
| 4,606,845 | 8/1986 | Romer et al. | 252/299.63 |
| 4,637,897 | 1/1987 | Kelly | 252/299.63 |
| 4,659,502 | 4/1987 | Fearon et al. | 252/299.61 |
| 4,664,840 | 5/1987 | Osman | 252/299.63 |
| 4,686,289 | 8/1987 | Huynh-ba et al. | 544/224 |
| 4,707,295 | 11/1987 | Pohl et al. | 252/299.62 |
| 4,710,315 | 12/1987 | Schad et al. | 252/299.63 |
| 4,724,097 | 2/1988 | Romer et al. | 252/299.63 |
| 4,776,973 | 10/1988 | Bofinger et al. | 252/299.63 |
| 4,808,333 | 2/1989 | Huyah-ba et al. | 252/299.66 |
| 4,820,839 | 4/1989 | Krause et al. | 544/316 |
| 4,834,904 | 5/1989 | Krause et al. | 252/299.01 |
| 4,846,998 | 7/1989 | Pohl et al. | 252/299.63 |
| 4,874,544 | 10/1989 | Yong et al. | 252/299.61 |
| 4,897,216 | 1/1990 | Reiffenrath et al. | 252/299.63 |
| 4,925,278 | 5/1990 | Buchecker et al. | 350/350.5 |
| 4,925,590 | 5/1990 | Reiffenrath et al. | 252/299.61 |
| 4,961,876 | 10/1990 | Demus et al. | 252/299.67 |
| 5,087,764 | 2/1992 | Reiffenrath et al. | 568/656 |

FOREIGN PATENT DOCUMENTS

| | | | |
|---|---|---|---|
| 0051738 | 3/1981 | European Pat. Off. | |
| 0133489 | 7/1984 | European Pat. Off. | |
| 1229870 | 10/1986 | Japan | 544/298 |
| WO88/02130 | 3/1988 | World Int. Prop. O. | |

Primary Examiner—Robert L. Stoll
Assistant Examiner—C. Harris
Attorney, Agent, or Firm—Millen, White, Zelano & Branigan

[57] ABSTRACT

Heterocyclic 1,2-difluorobenzene derivatives of the formula I

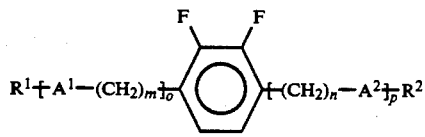

in which
R$^1$ and R$^2$, in each case independently of one another, are an alkyl groups (sic) having 1–15 C atoms in which, in addition, one or more CH$_2$ groups may be replaced by a divalent radical selected from the group comprising —O—, —S—, —CO—, —O—CO—, —CO—O—, —CH=CH— and —C≡C—, where two heteroatoms are not linked directly to one another,
A$^1$ and A$^2$, in each case independently of one another, are a 1,4-phenylene group which is unsubstituted or monosubstituted or polysubstituted by fluorine, and in which, in addition, one or two CH groups may be replaced by N, or are a 1,3,4-thiadiazole-2,5-diyl group or a trans-1,4-cyclohexylene group,
m and n are each 0 or 2,
o is 0 or 1, and
p is 0, 1 or 2,
where (o+p) is 1, 2 or 3 and, in the case where p=2, the A$^2$ groups and n may be identical or different with the proviso that at least one of the groups A$^1$ and A$^2$ is a 1,3,4-thiadiazole-2,5-diyl group or an unsubstituted or substituted 1,4-phenylene group in which one or two CH groups have been replaced by N,
are suitable as components of liquid-crystalline phases.

9 Claims, No Drawings

HETEROCYCLIC 1,2-DIFLUOROBENZENE DERIVATIVES

The invention relates to heterocyclic 1,2-difluorobenzene derivatives of the formula I

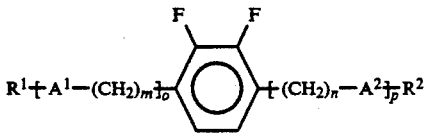

in which

R$^1$ and R$^2$, in each case independently of one another, are an alkyl groups (sic) having 1-15 C atoms in which, in addition, one or more CH$_2$ groups may be replaced by a divalent radical selected from the group comprising —O—, —S—, —CO—, —O—CO—, —CO—O—, —CH=CH— and —C≡C—, where two heteroatoms are not linked directly to one another, A$^1$ and A$^2$, in each case independently of one another, are a 1,4-phenylene group which is unsubstituted or monosubstituted or polysubstituted by fluorine, and in which, in addition, one or two CH groups may be replaced by N, or are a 1,3,4-thiadiazole-2,5-diyl group or a trans-1,4-cyclohexylene group, m and n are each 0 or 2, o is 0 or 1, and p is 0, 1 or 2, where (o+p) is 1, 2 or 3 and, in the case where p=2, the A$^2$ groups and n may be identical or different with the proviso that at least one of the groups A$^1$ and A$^2$ is a 1,3,4-thiadiazole-2,5-diyl group or an unsubstituted or substituted 1,4-phenylene group in which one or two CH groups have been replaced by N. The invention furthermore relates to liquid-crystalline phases containing compounds of the formula I, the use thereof as components of liquid-crystalline phases, and electrooptical display elements contain (sic) phases of this type.

For reasons of simplicity, Cyc below is a 1,4-cyclohexylene group, Pyd is a pyridine-2,5-diyl group, Pyr is a pyrimidine-2,5-diyl group, Pyn is a pyrazine-2,5-diyl group, Thi is a 1,3,4-thiadiazole-2,5-diyl group and Phe is 1,4-phenylene group, it being possible for these groups to be unsubstituted or substituted by one or two fluorine atoms. These groups are preferably unsubstituted.

PheF$_2$ is a group of the formula

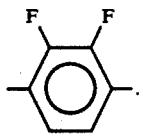

The compounds of the formula I can be used as components of liquid-crystalline phases, in particular for displays based on the principle of the twisted cell, the guest-host effect, the effect of deformation of aligned phases or the effect of dynamic scattering.

The compounds of the formula I are distinguished by a clearly negative anisotropy of the dielectric constant and, in an electrical field, are aligned with their longitudinal molecular axes perpendicular to the field direction.

This effect is known and is utilized to control the optical transparency in various liquid-crystal displays, for example in liquid-crystal cells of the light-scattering type (dynamic scattering), of the so-called DAP type (deformation of aligned phases) or ECB type (electrically controlled birefringence) or of the guest/host type (guest/host interaction).

In addition, compounds of the formula I are suitable as components of chiral tilted smectic phases. Chiral tilted smectic liquid-crystalline phases having ferroelectric properties can be prepared by adding a suitable chiral dope to base mixtures containing one or more tilted smectic phases (L. A. Veresnev et al., Mol. Cryst. Liq. Cryst. 89, 327 (1982); H. R. Brand et al., J. Physique 44 (lett.), L-771 (1983). Such phases can be used as dielectrics for rapidly switching displays based on the principle, described by Clark and Lagerwall, of SSFLC technology (N. A. Clark and S. T. Lagerwall, Appl. Phys. Lett. 36, 899 (1980); U.S. Pat. 4,367,924) on the basis of the ferroelectric properties of the chiral tilted phase.

A number of liquid-crystalline compounds having slightly negative dielectric anisotropy have hitherto already been synthesized. In contrast, only relatively few liquid-crystal components having a large negative anisotropy of the dielectric constant are known. In addition, the latter generally have disadvantages, such as, for example, poor solubility in mixtures, high viscosity, high melting points and chemical instability. There is therefore a demand for further compounds having negative dielectric anisotropy which permit the properties of mixtures to be further improved for a very wide variety of electrooptical applications.

Liquid-crystal compounds having a negative dielectric anisotropy and containing two or three rings linked via carboxyl groups or a covalent bond and containing one or more side groups, such as halogen, cyano or nitro groups, are known from DE 2,240,864, DE 2,613,293, DE 2,835,662, DE 2,836,086 and EP 023,728.

EP 084,194 gives a broad formula covering the compounds claimed here. However, no individual compounds of the formula according to the invention are mentioned. Those skilled in the art would thus be able neither to deduce in simple manner from the prior art possible syntheses for the compounds claimed nor to recognize that the compounds according to the invention have mesophase regions which are predominantly in a favourable location and are distinguished by a large negative anisotropy of the dielectricity with at the same time low viscosity.

Neither is there any indication of the possibility of using the compounds according to the invention in displays based on SSFLC technology, since the compounds claimed therein have low smectic tendencies.

Furthermore dibenzoic acid esters of 2,3-dichlorohydroquinone are known (for example Bristol et al., J. Org. Chem. 39, 3138 (1974) or Clanderman et al., J. Am. Chem. Soc. 97, 1585 (1975)), but these are monotropic or have very small mesophase ranges. The esters of 4-hydroxy-2,3-dichlorobenzoic acid described by Eidenschink et al. (Angew. Chem. 103 (1977)) likewise have only narrow mesophase ranges.

The 4-alkyl-2,3-dichlorophenyl-4'-alkylbicyclohexyl-4-carboxylic acid esters known from German Offenlegungsschrift 2,933,563 cannot be used industrially due to their high viscosity.

The invention had the object of indicating stable, liquid-crystalline or mesogenic compounds having a large negative anisotropy of the dielectricity and simultaneously low viscosity.

It has been found that the compounds of the formula I are preeminently suitable as components of liquid-crystalline phases. They can be used, in particular, to prepare stable liquid-crystalline phases having a broad mesophase range and comparatively low viscosity.

The compounds of the formula I are furthermore suitable as components of chiral tilted smectic liquid-crystalline phases.

In addition, the provision of compounds of the formula I very generally considerably broadens the range of liquid-crystalline substances which are suitable, from various applicational points of view, for the purpose of preparing liquid-crystalline mixtures.

The compounds of the formula I have a broad field of application. Depending on the choice of substituents, these compounds can be used as base materials from which liquid-crystalline phases are predominantly composed; however, it is also possible to add liquid-crystalline base materials from other classes of compounds to the compounds of the formula I in order, for example, to vary the dielectric and/or optical anisotropy and/or viscosity and/or the spontaneous polarization and/or the phase ranges and/or the tilt angle and/or the pitch of a dielectric of this type.

The compounds of the formula I are furthermore suitable as intermediates for the preparation of other substances which can be used as components of liquid-crystalline dielectrics.

In the pure state, the compounds of the formula I are colourless and form liquid-crystalline mesophases in a temperature range in a favourable location for electro-optical use. They are very stable chemically, thermally and to light.

The invention thus relates to the compounds of the formula I.

The invention additionally relates to the use of the compounds of the formula I as components of liquid-crystalline phases. The invention furthermore relates to liquid-crystalline phases containing at least one compound of the formula I, and to liquid-crystal display elements containing such phases. Phases of this type have particularly advantageous elastic constants, and, due to their low $\Delta\epsilon/\epsilon_\perp$ values, are particularly suitable for TFT mixtures.

Above and below, $R^1$, $R^2$, $A^1$, $A^2$, m and p are as defined, unless expressly stated otherwise.

Accordingly, the compounds of the formula I include compounds having 2 rings, of the sub-formulae Ia and Ib, compound (sic) having 3 rings, of the subformulae Ic to Ih, and compounds having 4 rings, of the sub-formulae Ij to Im:

$R^1$—PheF$_2$—$A^2$—$R^2$   Ia $R^1$—PheF$_2$—CH$_2$CH$_2$—$A^2$—$R^2$   Ib $R^1$—PheF$_2$—$A^2$—$A^2$—$R^2$   Ic $R^1$—PheF$_2$—$A^2$—CH$_2$CH$_2$—$A^2$—$R^2$   Id $R^1$—PheF$_2$—CH$_2$CH$_2$—$A^2$—$A^2$—$R^2$   Ie $R^1$—$A^1$PheF$_2$—$A^2$—$R^2$   If $R^1$—$A^1$—CH$_2$CH$_2$—PheF$_2$—$A^2$—$R^2$   Ig $R^1$—$A^1$—CH$_2$CH$_2$—PheF$_2$—CH$_2$CH$_2$—$A^2$—$R^2$   Ih $R^1$—$A^1$—PheF$_2$—$A^2$—$A^2$—$R^2$   Ij $R^1$—$A^1$—PheF$_2$—CH$_2$CH$_2$—$A^2$—$A^2$—$R^2$   Ik $R^1$—$A^1$—CH$_2$CH$_2$—PheF$_2$—$A^2$—$A^2$$R^2$   Il $R^1$—$A^1$—PheF$_2$—$A^2$—CH$_2$CH$_2$—$A^2$—$R^2$   Im

Of these, those of the sub-formulae Ia, Ic, Id, If and Ig are particularly preferred.

In the compounds of the formulae above and below, $R^1$ and $R^2$ are preferably alkyl or alkoxy.

Additionally preferred compounds are those of the formulae above and below in which one of the radicals $R^1$ and $R^2$ is alkenyl or oxaalkyl (for example alkoxymethyl).

In the formulae above and below, $R^1$ and $R^2$ preferably have 2–12 C atoms, in particular 3–10 C atoms. It is also possible for one or two CH$_2$ groups in $R^1$ and $R^2$ to have been replaced. It is preferred that only one CH$_2$ group has been replaced, by —O— or —CH=CH—.

In the formulae above and below, $R^1$ and $R^2$ are preferably alkyl, alkoxy or another oxaalkyl group, furthermore also alkyl groups in which one or two CH$_2$ groups may be replaced by —CH=CH—.

If $R^1$ and $R^2$ are alkyl radicals in which, in addition, one ("alkoxy" or "oxaalkyl") or two ("alkoxylakoxy" (sic) or "dioxaalkyl") non-adjacent CH$_2$ groups may be replaced by O atoms, they can be straight-chain or branched. They are preferably straight-chain, have 2,3,4,5,6 or 7 C atoms and are accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (sic) (=methoxymethyl), 2-(=ethoxymethyl) or 3-oxabutyl (sic) (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, or 2,4-dioxapentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-, 3,6- or 4,6-dioxaheptyl.

If $R^1$ and $R^2$ are an alkyl radical in which one CH$_2$ group has been replaced by —CH=CH—, the trans form is preferred. This alkenyl radical can be straight-chain or branched. It is preferably straight-chain and has 2–10 C atoms. It is accordingly particularly vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-,-2-, -3-, -4-, -5-, -6-, -7- or -8-enyl, or dec-1-,-2-, -3-, -4-, -5-, -6-, -7-, -8- or -9-enyl.

Compounds of the formula I having branched wing groups $R^1$ and/or $R^2$ may occasionally be of importance due to better solubility in the customary liquid-crystalline base materials, but in particular as chiral dopes if they are optically active. Smectic compounds of this type are suitable as components for ferroelectric materials.

Branched groups of this type generally contain not more than one chain branch. Preferred branch radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-mathylbutyl, 3-oxa-4-methylpentyl, 4-methylhexyl, 2-nonyl, 2-decyl, 2-dodecyl and 6-methyloctoxy.

The formula I covers the racemates of these compounds and the optical antipodes, and mixtures thereof.

m and n are preferably 0. Furthermore preferred compounds are those of the formula I which contain one —CH$_2$CH$_2$— group, i.e. m or n is simply 1.

(o+p) is preferably 1 or 2. If o=0 and R$^1 \neq$n-alkoxy, (o+p) is preferably 2 or 3.

The groups A1 and A2 are preferably Cyc, Phe, Pyd, Pyr, Pyn or Thi. Preferably, only one of the groups A$^1$ and A$^2$ is Cyc, Pyd, Pyr, Pyn or Thi.

Particularly preferred meanings of $$\ce{+A^1-(CH_2)_m\frac{1}{o}PheF_2+(CH_2)_n-A^2\frac{1}{p}}$$

are the groups 1 to 28 below:

| | |
|---|---|
| Pyd-PheF | 1 |
| Pyr-PheF$_2$ | 2 |
| Pyn-PheF$_2$ | 3 |
| Thi-PheF$_2$ | 4 |
| Pyd-PheF$_2$-Phe | 5 |
| Pyr-PheF$_2$-Phe | 6 |
| Pyn-PheF$_2$-Phe | 7 |
| Thi-PheF$_2$-Phe | 8 |
| Pyd-Phe-PheF$_2$ | 9 |
| Pyr-Phe-PheF$_2$ | 10 |
| Pyn-Phe-PheF$_2$ | 11 |
| Thi-Phe-PheF$_2$ | 12 |
| Phe-Pyd-PheF$_2$ | 13 |
| Phe-Pyr-PheF$_2$ | 14 |
| Phe-Pyn-PheF$_2$ | 15 |
| Phe-Thi-PheF$_2$ | 16 |
| PheF$_2$-Pyd-Cyc | 17 |
| PheF$_2$-Pyr-Cyc | 18 |
| PheF$_2$-Pyn-Cyc | 19 |
| PheF$_2$-Thi-Cyc | 20 |
| Pyd-PheF$_2$-Cyc | 21 |
| Pyr-PheF$_2$-Cyc | 22 |
| Pyn-PheF$_2$-Cyc | 23 |
| Thi-PheF$_2$-Cyc | 24 |
| Pyd-PheF$_2$-CH$_2$CH$_2$-Cyc | 25 |
| Pyr-PheF$_2$-CH$_2$CH$_2$-Cyc | 26 |
| Pyn-PheF$_2$-CH$_2$CH$_2$-Cyc | 27 |
| Thi-PheF$_2$-CH$_2$CH$_2$-Cyc | 28 |

Of the compounds of the formulae I and Ia to Im, those are preferred in which at least one of the radicals present therein has one of the preferred meanings indicated.

A smaller group of particularly preferred substances is that of the formulae:

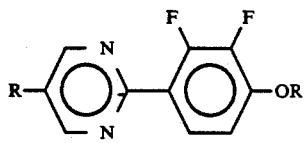

A

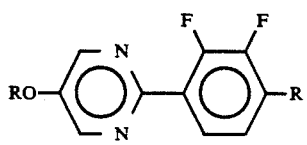

B

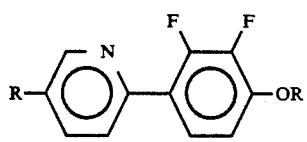

C

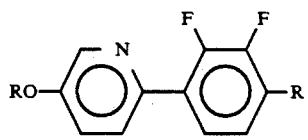

D

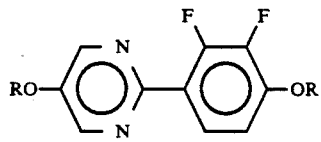

E

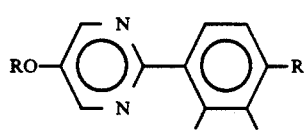

F

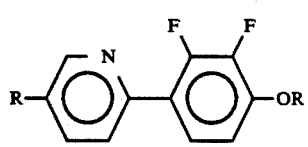

G

In these formulae, R is, in each case independently of one another, straight-chain or monobranched (preferably a methyl branch) alkyl having 3 to 12 C atoms in which, in addition, one CH$_2$ gorup which is not linked to O may be replaced by —O— or —CH=CH—.

R is preferably alkyl, oxaalkyl or alkenyl, oxaalkyl or alkenyl preferably having 3 to 12, in particular 5 to 12, C atoms. The groups R are ppreferably straight-chain.

Particularly preferred compounds according to the invention are those of the sub-formula I2

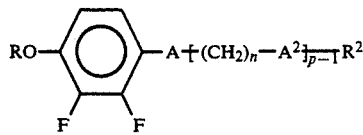

in which R is an alkyl group having 1 to 15 C atoms in which, in addition, one or more CH$_2$ groups may be replaced by a divalent radical selected from the group comprising —O—, —S—, —CO—, —O—CO—, —CO—O—, —CH=CH— and —C≡C—, where two heteroatoms are not linked directly to one another. p is 1 or 2. n, A$^2$ and R$^2$ have the abovementioned meaning. A is a 1,3,4-thiadiazole-2,5-diyl-, pyrimidine-2,5-diyl, pyridine--2,5-diyl or pyrazine-2,6-diyl group. A is preferably A particularly preferred smaller group of compounds is that of the formula I1

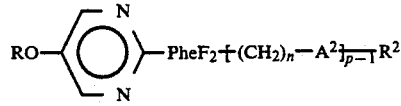

in which R is an alkyl group having 1 to 15 C atoms in which, in addition, one or more CH$_2$ groups may be replaced by a divalent radical selected from the group comprising —O—, —S—, —CO—, —O—CO—, —CO—O—, —CH=CH— and —C≡C—, where two heteroatoms are not linked directly to one another. p is 1 or 2. PheF$_2$, n, A$^2$ and R$^2$ have the abovementioned meaning. The compounds of the formula I1 can be prepared as indicated in scheme 1 below:

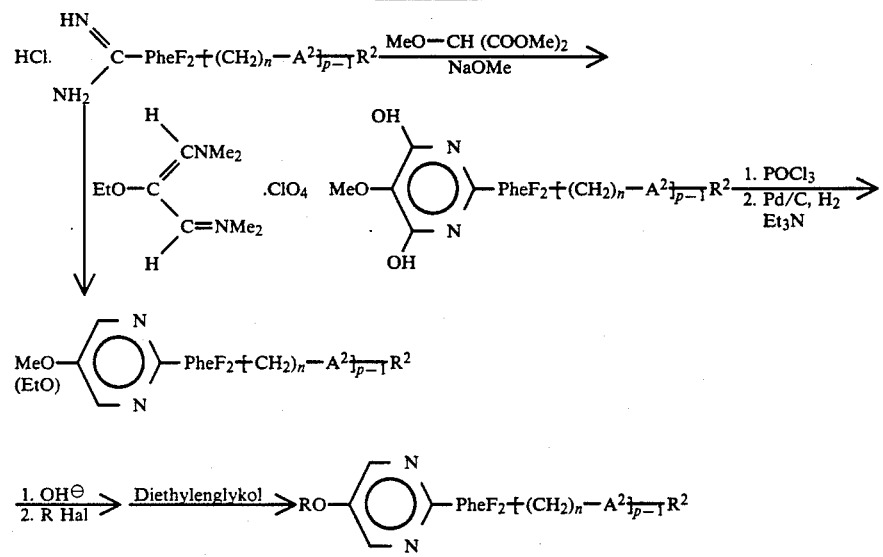

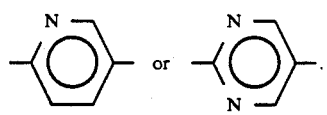

Possible syntheses of further preferred compounds are indicated in the schemes below:

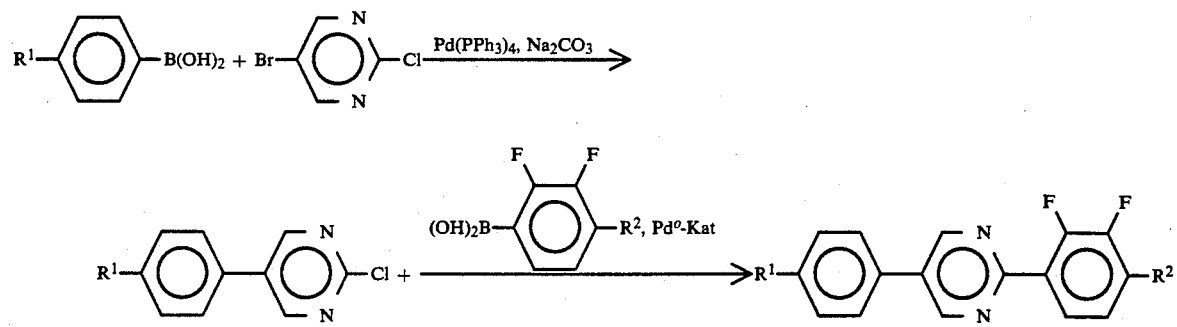

Scheme 3
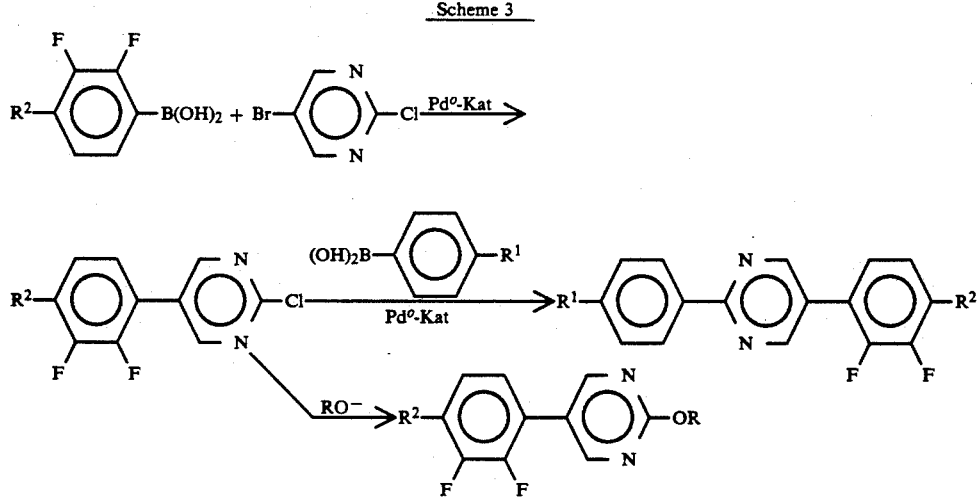
Scheme 4
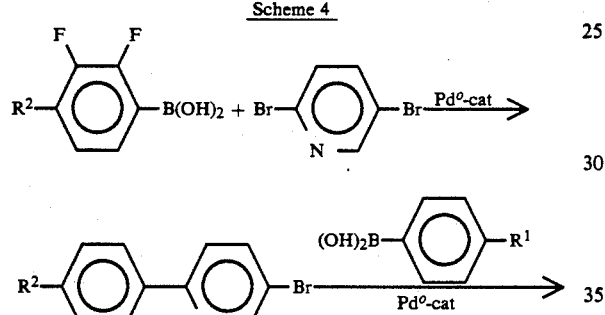
Scheme 5 -continued
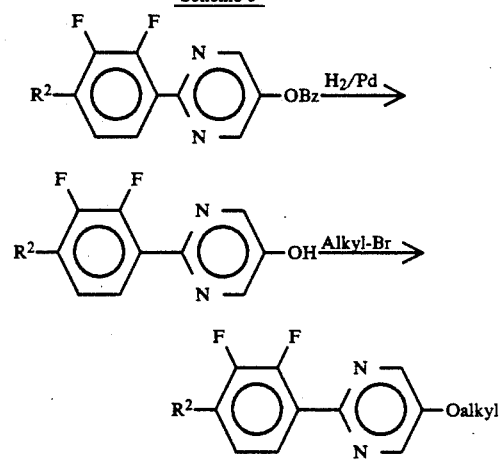
Scheme 5
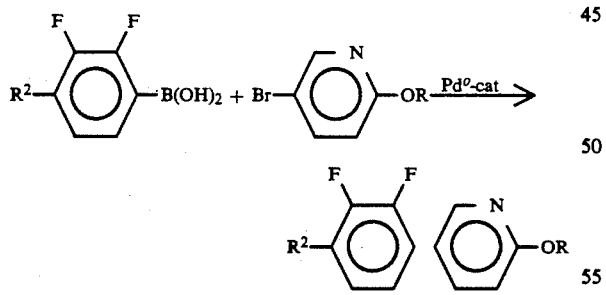
Scheme 6
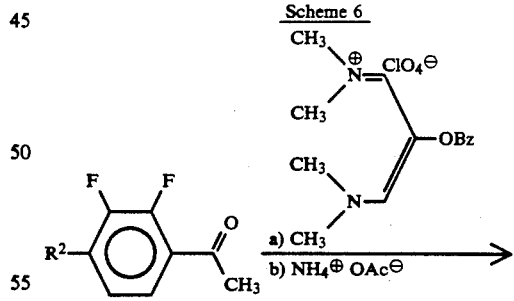
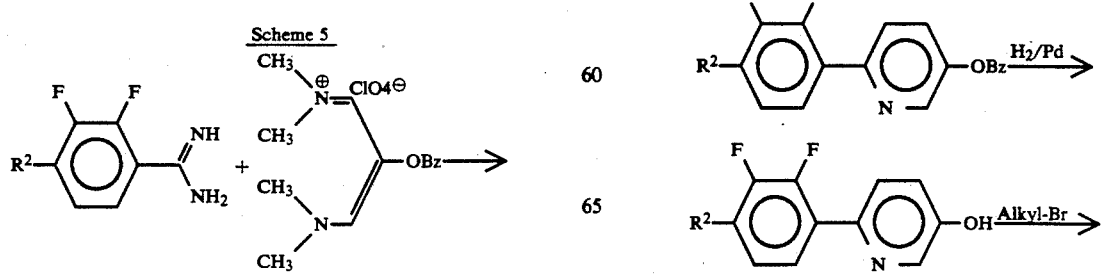

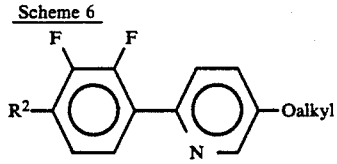
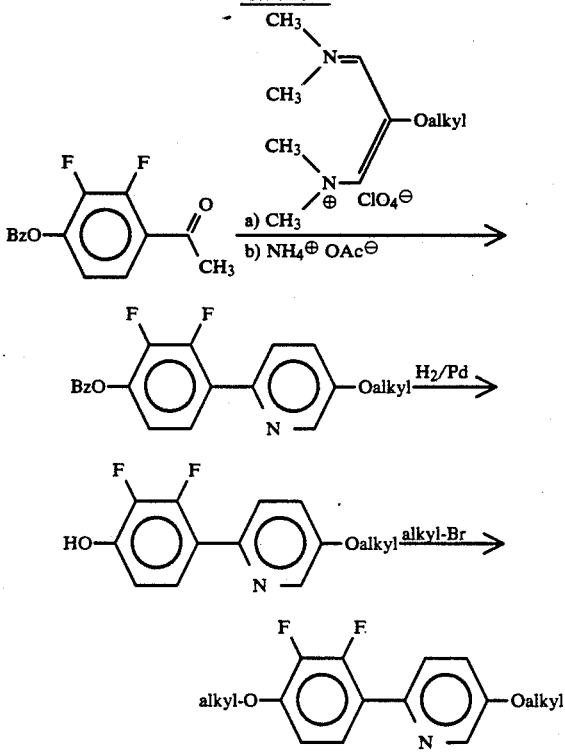

The compounds of the formula I are prepared by methods which are known per se, as described in the literature (for example in the standard works such as Houben-Weyl, Methoden der Organischen Chemie [Methods of organic chemistry], Georg-Thieme-Verlag, Stuttgart), to be precise under reaction conditions which are known and suitable for the reactions mentioned. Use can also be made here of variants which are known per se, but are not described in greater detail here.

If desired, the starting materials can also be formed in situ by not isolating them from the reaction mixture, but instead immediately reacting them further to form the compounds of the formula I.

Compounds of the formula I or precursors thereof are accessible starting from 1,2-difluorobenzene. The latter is metallated by known processes (for example A. M. Roe et al., J. Chem. Soc. Chem. Comm., 22, 582 (1965)) and reacted with the appropriate electrophile. This reaction sequence can be carried out a second time using a suitable electrophile with the 1-substituted 2,3-difluorobenzene obtained in this way, to give 1,4-disubstituted 2,3-difluorobenzenes which are suitable for the syntheses of the heterocyclic compounds. 1,2-Difluorobenzene or 1-substituted 2,3-difluorobenzene is reacted with phenyllithium, lithium tetramethylpiperidine, or n-, sec- or tert-butyllithium at temperatures of from −100° C. to +50° C., preferably −78° C. to 0° C., in an inert solvent, such as diethyl ether, tetrahydrofuran, dimethoxyethane, tert-butyl methyl ether or dioxane, hydrocarbons, such as hexane, heptane, cyclohexane, benzene or toluene, or mixtures of these solvents, if appropriate with addition of a complexing agent, such as tetramethylethylenediamine (TMEDA) or hexamethylphosphoric triamide.

The lithium 2,3-difluorophenyl compounds are reacted with the appropriate electrophiles at −100° C. to 0° C., preferably at −50° C. Suitable electrophiles are aldehydes, ketones, nitriles, epoxides, carboxylic acid derivatives, such as esters, anhydrides or halides, haloformic acid esters or carbon dioxide. Further details can be obtained from German Offenlegungsschrift 3,807,910.

For reaction with aliphatic or aromatic halogen compounds, the lithium 2,3-difluorophenyl compounds are transmetallated and coupled with transition-metal catalysis. Zinc 2,3-difluorophenyl compounds (cf. German Offenlegungsschrift 3,632,410) or titanium 2,3-difluorophenyl compounds (cf. German Offenlegungsschrift 3,736,489) are particularly suitable for this purpose.

The heterocyclic structural elements can be introduced on the one hand by converting precursors which already contain these structural elements into compounds of the formula I by known methods. On the other hand, however, heterocyclic radicals can be produced in appropriately structured precursors or substructure units of the compounds of the formula I by methods known per se.

Thus, for example, 2,5-disubstituted 1,3,4-thiadiazoles can be prepared by reacting N,N,-diacylhydrazines with customary thiation reagents, such as P₄S₁₀ or Lawesson,s reagent. The N,N'-diacylhydrazines are themselves accessible by known methods from the corresponding carboxylic acids, it being possible for the carboxylic acids having a 2,3-difluoro-1,4-phenylene structural element as described above to be obtained by reacting appropriate metallated precursors with carbon dioxide.

The 2,5-disubstituted pyrimidines can be prepared, for example, by reacting appropriate amidine hydrochlorides (which can be prepared from the corresponding carboxylic acids) with malondialdehyde tetramethyl acetals by methods known per se. The 2,5-disubstituted pyridines can be obtained by coupling organometallic zinc compounds with appropriate bromopyridine derivatives in accordance with German Offenlegungsschrift 3,632,410. The 2,5-disubstituted pyrazines can be obtained by condensation of suitably substituted ethylenediamines with glyoxal derivatives, oxidation of the dihydro compounds using atmospheric oxygen or other oxidants, and isolation of the 2,5-disubstituted pyrazines desired from the resultant mixture of 2,5- and 2,6-disubstitution products. The 3,6-disubstituted pyridazines are accessible by reacting 1,4-diketones (prepared, for example, by the method of Stetter by thiazolium salt-catalysed addition of an aldehyde to an α,β-unsaturated ketone) and subsequent oxidation of the dihydropyr-idazine using atmospheric oxygen or other oxidants such as potassium nitrite or chromic acid in glacial acetic acid.

The synthesis of some particularly important hydroxyl intermediates is described below:

a) 5-alkyl-2-(2,3-difluoro-4-hydroxyphenyl)pyridines can be obtained by reacting 2,3-difluoro-4-benzyloxybenzamidine hydrochloride with 2-alkyl-3-ethoxyacroleins or with 2-alkylated malonaldehyde tetraacetals or appropriately substituted vinylogous formamidinium salts (R. M. Wagner and CH. Jutz, Chem. Ber. 104 2975 (1971), by preferably heating the components in DMF (dimethylformamide) and subsequently removing the protecting group hydrogenolytically.

b) 5-Hydroxy-2-(2,3-difluoro-4-alkylphenyl)pyrimidines and 5-hydroxy-2-(2,3-difluoro-4-alkoxyphenyl)pyrimidines can be obtained by condensation of 4-alkyl- or 4-alkoxy-2,3-difluorobenzamidine hydrochloride with 2-benzyloxytrimethinium perchlorate (A. Holy, Z. Arnold; Collection Czechoslov. Chem. Comm. 38 1371–1380 (1973), or 2-benzyloxy-3-dimethylaminoacrolein (H. Horstmann et al., Arzneimittelforsch. 11 682 (1961) and subsequent hydrogenolysis of the benzyl group.

c) 5-Hydroxy-2-(2,3-difluoro-4-alkylphenyl)pyridines and 5-hydroxy-2-(2,3-difluoro-4-alkoxyphenyl)pyridines can be obtained from 2-benzyloxytrimethinium salt by condensation with 4-alkyl- or 4-alkoxy-2,3-difluoroacetophenones, reaction with NH$_3$/NH$_4$Cl or ammonium acetate.

Analogously to the procedures of Ch. Jutz et al. (Liebigs Ann. Chem. 1975 874–900) and subsequent hydrogenolysis, or from 4-alkyl- or 4-alkoxy-2,3-difluorophenylboric acid by coupling with 5-acetoxy-2-bromopyridine (obtainable from 5-hydroxy-2-bromopyridine by esterification) in the presence of a Pd catalyst in accordance with the work of Suzuki et al. (Synth. Commun. 11 513–19 (1981)).

d) 5-Alkoxy-2-(2,3-difluoro-4-hydroxyphenyl)pyridines can be obtained by coupling 2,3-difluoro-4-benzyloxyphenylboric acid with 5-alkoxy-2-bromopyridine in accordance with the abovementioned literature and subsequent hydrogenolysis.

e) 5-Alkyl-2-(2,3-difluoro-4-hy-droxyphenyl)pyridines can be obtained by coupling 2-bromo-5-methylpyridine with 2,3-difluoro-4-benzy-loxyphenylboric acid and a Pd catalyst under the abovementioned conditions, extending the chain of the methyl group by deprotonation using LDA as base ($-65°$ C.) and alkylation using an alkylbromide and hydrogenolysis.

f) 5-Alkyl-2-(2,3-difluoro-4-hydroxyphenyl)pyrimidines and 5-alkoxy-2-(2,3-difluoro-4-hydroxyphenyl)pyrimidines can be prepared by customary condensation of 2,3-difluoro-4-benzyloxybenzamidine with 2-alkylmalonaldehyde tetraacetals or 2-alkyl-3-ethoxyacroleins or 2,3-dialkoxyacroleins or the corresponding immonium salts or alkoxytrimethinium salts, and subsequent hydrogenolysis.

In addition to one or more compounds according to the invention, the liquid-crystalline media according to the invention preferably contain, as further components, 2 to 40, in particular 4 to 30, components. Besides one or more compounds according to the invention, these media very particularly preferably contain 7 to 25 components. These further components are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexyl- phenyl benzoate, cyclohexanecarboxylate and cyclohexylcyclohexanecarboxylate, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-cyclohexyl-2-(4-phenylcyclohexyl)ethanes, 1-cyclohexyl-2-biphenylylethanes, 1-phenyl-2-cyclohexylphenyl-ethanes, optionally halogenated stilbenes, benzyl phenyl ethers, tolans and substituted cinnamic acids. The 1,4-phenylene groups in these compounds may also be fluorinated.

The most important compounds which are suitable as further components of media according to the invention can be characterized by the formulae 1, 2, 3, 4 and 5:

   1

   2

   3

   4

   5

In formulae 1, 2, 3, 4 and 5, L and E, which may be identical or different and are in each case independent of one another, are a divalent radical from the group formed from —Phe—, —Cyc—, —Phe—Phe—, —Phe—Cyc—, —Cyc—Cyc—, —Pyr—, —Dio—, —G—Phe— and —G—Cyc— and the mirror images thereof, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radical (sic) L and E is preferably Cyc, Phe or Pyr. E is preferably Cyc, Phe or Phe-Cyc. The media according to the invention preferably contain one or more components selected from the compounds of the formulae 1, 2, 3, 4 and 5, in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and, if appropriate, one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R", in each case independently of one another, are alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, F, Cl or —NCS; in these formulae, R has the meaning indicated in the case of the compounds of the sub-formulae 1a to 5a and is preferably alkyl or alkenyl. However, other variants of the proposed substituents in the compounds of the formulae 1, 2, 3, 4 and 5 are common. Many such substances and also mixtures thereof are commercially available. All these substances can be obtained by methods known from the literature or analogously thereto.

Besides components from the group comprising the compounds 1a, 2a, 3a, 4a and 5a (group 1), the media according to the invention preferably also contain components from the group comprising the compounds 1b, 2b, 3b, 4b and 5b (group 2), whose proportions are preferably as follows:

Group 1: 20 to 90%, in particular 30 to 90%,
Group 2: 10 to 80%, in particular 10 to 50%, the sum of the proportions of the compounds according to the invention and of the compounds from groups 1 and 2 adding up to 100%.

The media according to the invention preferably contain 1 to 40%, in particular preferably 5 to 30%, of compounds according to the invention. Additionally preferred media are those which contain more than 40%, in particular 45 to 90%, of compounds according to the invention. The media preferably contain three, four or five compounds according to the invention.

The media according to the invention are prepared in a manner customary per se. In general, the components are dissolved in one another, preferably at elevated temperature. By means of suitable additives, the liquid-crystalline phases according to the invention can be modified in a manner such that they can be used in all types of liquid-crystal display elements disclosed hitherto. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the preparation of coloured guest/host systems, or substances can be added to modify the dielectric anisotropy, the viscosity and/or the orientation of the nematic phases.

The examples below are intended to illustrate the invention without representing a limitation. mp.=melting point, cp.=clear point. Above and below, percentages are percent by weight; all temperatures are given in degrees Celsius. "Customary work-up" means that water is added, the mixture is extracted with methylene chloride, the organic phase is separated off, dried and evaporated, and the product is purified by crystallization and/or chromatography.

In addition, the abbreviations have the following meanings:

C: crystalline-solid state, S: smectic phase (the index characterizes the phase type), N: nematic state, Ch: cholesteric phase, I: isotropic phase. The number between two symbols indicates the conversion temperature in degrees Celsius.

EXAMPLE 1

1.0 mol of 2,3-difluoro-4-octyloxybenzoylchloride (which can be prepared by alkylation of 2,3-difluorophenol using octyl bromide/potassium carbonate in dimethylformamide (DMF), metallation of the 2,3-difluorooctyloxybenzene in the 4-position using butyllithium/tetramethylethylenediamine in tetrahydrofuran (THF) at $-70°$ to $-80°$, reaction with dry ice, and reaction of the acid with thionyl chloride) in 150 ml of pyridine are treated at 20°-25° with stirring with 0.1 mol of decanoyl hydrazide. The mixture is stirred for a further 2 hours and poured into 750 ml of water, and the precipitate is filtered off with suction, washed with water and dried.

The bisacyl compound is dissolved in the necessary amount of THF with warming and refluxed for 3 hours with 1.1 times the molar amount of Lawesson reagent. The majority of the solvent is removed by distillation, water is added, and the mixture is rendered alkaline using sodium hydroxide solution. The 2-(2,3-difluoro-4-octyloxyphenyl)-5-nonyl-1,3,4-thiadiazole which precipitates is filtered off with suction, washed with water, dried and recrystallized from ethanol.

EXAMPLE 2

Analogously to the preceding example, 2-(2,3-difluoro-4-heptylbiphenyl)-5-(4-hexyloxyphenyl)-1,3,4-thiadiazole is obtained by reacting 4-hexyloxybenzahydrazide with 2,3-difluoro-4-heptylbenzoyl chloride, (prepared by reacting o-difluorobenzene with butyllithium in the presence of potassium tertiary-butylate at $-90°$ to $100-$ in tetrahydrofuran, alkylation of the potassium compound formed using heptyl bromide/1,3-dimethyltetrahydro-2-(1H)-pyrimidinone (DMPU), isolation of the 2,3-difluoroheptylbenzene, re-metallation using butyllithium, subsequent reaction with solid carbon dioxide and heating of the acid with thionyl chloride) and subsequent ring closure using Lawesson reagent.

The following are prepared analogously:
2-(2,3-difluoro-4-octyloxyphenyl)-5-nonyl-1,3,4-thiadiazole
2-(2,3-difluoro-4-nonyloxyphenyl)-5-nonyl-1,3,4-thiadiazole
2-(2,3-difluoro-4-decyloxyphenyl)-5-nonyl-1,3,4-thiadiazole
2-(2,3-difluoro-4-heptyloxyphenyl)-5-nonyl-1,3,4-thiadiazole
2-(2,3-difluoro-4-hexyloxyphenyl)-5-nonyl-1,3,4-thiadiazole
2(2,3-difluoro-4-octyloxyphenyl)-5-octyl-1,3,4-thiadiazole
2-(2,3-difluoro-4-nonyloxyphenyl)-5-octyl-1,3,4-thiadiazole
2-(2,3-difluoro-4-decyloxyphenyl)-5-octyl-1,3,4-thiadiazole
2-(2,3-difluoro-4-heptyloxyphenyl)-5-octyl-1,3,4-thiadiazole
2-(2,3-difluoro-4-hexyloxyphenyl)-5-octyl-1,3,4-thiadiazole
2-(2,3-difluoro-4-octyloxypheny-1)-5-heptyl-1,3,4-thiadiazole
2-(2,3-difluoro-4-nonyloxyphenyl)-5-heptyl-1,3,4-thiadiazole
2-(2,3-difluoro-4-decyloxyphenyl)-5-heptyl-1,3,4-thiadiazole
2-(2,3-difluoro-4-heptyloxyphenyl)-5-heptyl-1,3,4-thiadiazole
2-(2,3-difluoro-4-hexyloxyphenyl)-5-heptyl-1,3,4-thiadiazole

EXAMPLE 3

2-[2,3-difluoro-4-(4-pentylphenyl)phenyl]-5-butyl-1,3,4-thiadiazole is obtained by reacting 2,3-difluoro-4,-pentylbiphenyl-4-carbonyl chloride and valerohydrazide and a subsequent ring closure using Lawesson reagent.

The biphenyl ester required is obtained as follows: o-difluorobenzene is lithiated at $-70°$ to $-80°$, the lithiation product is reacted at this temperature with 4-pentylcyclohexanone, the alcohol produced is dehydrated, and the cyclohexene derivative is aromatized by refluxing with 2,3-dichloro-5,6-dicyano-p-benzoquinone (DDQ) in toluene. The 2,3-difluoro-4'-pentylbiphenyl is re-metallated, and solid carbon dioxide is added. The acid is subsequently esterified using methanol and sulphuric acid.

EXAMPLE 4

2,3-Difluoro-4-ethoxybenzoyl chloride (prepared as described in Example 1 for the octyloxy compound) is reacted in pyridine with trans-4-propylcyclohexanecarbohydrazide, and the bisacyl compound is converted into 2-(2,3-difluoro-4-ethoxyphenyl)-5-(trans-4-propylcyclohexyl)-1,3,4-thiadiazole using Lawesson reagent.

EXAMPLE 5

0.1 mol of 2,3-difluoro-4-nonyloxybenzamidine hydrochloride (prepared from 2,3-difluoro-4-nonyloxybenzoyl chloride by conversion into the amide, dehydration thereof to form the nitrile, reaction of the nitrile with ethanol and hydrogen chloride gas, and subsequent reaction of the imidoester with ammonia), 0.1 mol of nonylmalonaldehyde tetramethyl acetal and 50 ml of DMF are heated at 150° for 12 hours. The reaction mixture is subsequently taken up in dichloromethane, washed with sodium bicarbonate solution and water until neutral and dried, and the solvent is removed by distillation. The residue obtained is 2-(2,3-difluoro-4-nonyloxyphenyl)-5-nonylpyrimidine, which is crystallized from ethanol: C 41 $S_c$ 54 I.

The following are prepared analogously:
2-(2,3-difluoro-4-decyloxyphenyl)-5-nonylpyrimidine
2-(2,3-difluoro-4-octyloxyphenyl)-5-nonylpyrimidine
2-(2,3-difluoro-4-heptyloxyphenyl)-5-nonylpyrimidine C 47 $S_c$ 52 I
2-(2,3-difluoro-4-hexyloxyphenyl)-5-nonylpyrimidine
2-(2,3-difluoro-4-decyloxyphenyl)-5-decylpyrimidine
2-(2,3-difluoro-4-nonyloxyphenyl)-5-decylpyrimidine
2-(2,3-difluoro-4-octyloxyphenyl)-5-decylpyrimidine
2-(2,3-difluoro-4-heptyloxyphenyl)-5-decylpyrimidine
2-(2,3-difluoro-4-hexyloxyphenyl)-5-decylpyrimidine
2-(2,3-difluoro-4-decyloxyphenyl)-5-octylpyrimidine
2-(2,3-difluoro-4-nonyloxyphenyl)-5-octylpyrimidine
2-(2,3-difluoro-4-octyloxyp-henyl)-5-octylpyrimidine
2-(2,3-difluoro-4-heptyloxyphenyl)-5-octylpyrimidine
2-(2,3-difluoro-4-hexyloxyphenyl)-5-octylpyrimidine
2-(2,3-difluoro-4-decyloxyphenyl)-5-heptylpyrimidine
2-(2,3-difluoro-4-nonyloxyphenyl)-5-heptylpyrimidine C 46 $S_c$ (34) N (45) I
2-(2,3-difluoro-4-octyloxyphenyl)-5-heptylpyrimidine
2-(2,3-difluoro-4-heptyloxyphenyl)-5-heptylpyrimidine C 36 $S_c$ (33) N 42 I
2-(2,3-difluoro-4-hexyloxyphenyl)-5-heptylpyrimidine
2-(2,3-difluoro-4-decyloxyphenyl)-5-hexylpyrimidine
2-(2,3-difluoro-4-nonyloxyphenyl)-5-hexylpyrimidine
2-(2,3-difluoro-4-octyloxyphenyl)-5-hexylpyrimidine
2-(2,3-difluoro-4-heptyloxyphenyl)-5-hexylpyrimidine
2-(2,3-difluoro-4-hexyloxyphenyl)-5-hexylpyrimidine

EXAMPLE 6

Reaction of 2,3-difluoro-4,-propylbiphenyl-4-carbamidine hydrochloride (the biphenylcarboxylic acid necessary for this is obtained analogously to Example 3) with butylmalonaldehyde tetramethyl acetal in DMF gives, after customary work-up, 2,3-difluoro-4-(5-butylpyrimidin-2-Yl)-4'-propylbiphenyl.

EXAMPLE 7

Reaction of O-difluorobenzene (sic) with butyllithium in the presence of potassium tertiary-butylate at −90° to −100° in tetrahydrofuran, alkylation of the potassium compound formed using 1-bromo-2-(trans-4-pentylcyclohexyl)ethane/DMPU, isolation of the cyclohexylphenylethane derivative, a re-metallation using butyllithium and subsequent reaction with a solid carbon dioxide gives 2,3-difluoro-4-[2-(trans-4-pentylcyclohexyl)ethyl]benzoic acid. The latter is converted, in a customary manner, into the amidine hydrochloride, which, on reaction with hexylmalondialdehyde tetramethyl acetal, gives 2-{2,3-difluoro-4-[2-(trans-4-pentylcyclohexyl)ethyl]phenyl}-5-hexylpyrimidine.

EXAMPL 8

A solution of 0.1 m of n-BuLi in hexane is added dropwise over the course of half an hour at −60° to −70° C. with stirring to a solution of 0.1 m of 2,3-difluorononyloxybenzene in 200 ml of THF. The mixture is stirred at this temperature for a further 2 hours, and a solution of 0.05 m of ZnBr$_2$ (anhydrous) in 100 ml of THF is subsequently added dropwise at the same temperature. After a further hour, a solution of 0.1 m of 2-bromo-5-methylpyridine and 2 m% (0.002 m) of bis-triphenylphosphinenickel(II) chloride, dissolved in 50 ml of THF, is slowly added, and the mixture is stirred for a further 16 hours, the temperature being allowed to slowly reach room temperature. Water is added and the mixture is worked up extractively. The crude product is purified by recrystallization and chromatography, to give 2-(2,3-difluoro-4-nonyloxyphenyl)-5-methylpyridine.

The following are prepared analogously:
2-(2,3-difluoro-4-nonyloxyphenyl)-5-octylpyridine
2-(2,3-difluoro-4-octyloxyphenyl)-5-octylpyridine C 20 $S_c$ 26 N 37.9 I
2-(2,3-difluoro-4-octyloxyphenyl)-5-nonylpyridine
2-(2,3-difluoro-4-nonyloxyphenyl)-5-nonylpyridine
2-(2,3-difluoro-4-hexyloxyphenyl)-5-nonylpyridine

EXAMPLE 9

60 ml of 2 M Na$_2$CO$_3$ solution and 0.5 g of Pd(PPh$_3$)$_4$ are added to a solution of 16.2 g of 4-n-octyl-2,3-difluorophenylboric acid (prepared by lithiation of 2,3-difluorooctylbenzene, reaction with trimethyl borate and subsequent hydrolysis of the boric acid ester using dilute hydrochloric acid) and 16.7 g of 2-p-bromophenyl-5-n-heptylpyrimidine in a mixture of 100 ml of toluene and 40 ml of ethanol. The emulsion is refluxed for 18 hours with stirring, and the organic phase is worked up in a customary manner to give 2-(2,3-difluoro-4-n-octylbiphenyl-4,-yl)-5-n-heptylpyrimidine, C 64 $S_c$ 90 N 118 I.

EXAMPLE 10

2,5-bis-(2,3-difluoro-4-n-pentylphenyl)pyrazine C 117 N 120 I, is obtained analogously to Example 9 from 27.4 g of 4-n-pentyl-2,3-difluorophenylboric acid and 7.5 g of 2,5-dichloropyrazine.

EXAMPLE 11

2-Chloro-5-(4-n-octyl-2,3-difluorophenyl)pyrimidine is obtained analogously to Example 9 from 2.7 g of 2-chloro-5-bromopyridine (prepared by reacting 2-hydroxypyrimidine hydrochloride with bromine in water, evaporating the water and boiling the dry residue with POCl₃) and 3.8 g of 4-n-octyl-2,3-difluorophenylboric acid, and the product is reacted with p-n-pentylboric acid, likewise analogously to Example 9 to give 2-(p-n-pentylphenyl)-5-(4-n-octyl-2,3-difluorophenyl)-pyrimidine, C82.S$_C$101 S$_A$105 N 121 I

EXAMPLE 12

0.1 mol of 2-(2,3-difluoro-4-octyloxyphenyl)-5-hydroxypyrimidine (prepared by reacting 2,3-difluoro-4-octyloxybenzamidine with 2-benzyloxytrimethinium perchlorate [A. Holy and Z. Arnold, Coll. Czech. Chem. Commun. 1372 (1973)] and subsequently hydrogenolysing the benzyl ether), 0.11 mol of potassium carbonate and 0.11 mol of 1-bromononane are refluxed for 18 hours at 120° in 100 ml of dimethylformamide with stirring. The mixture is allowed to cool, the inorganic salts are removed by filtration, and the majority of the dimethylformamide is removed from the filtrate by distillation. The solution of the residue in dichloromethane is washed with water and dried. After the solvent has been stripped off, the 2-(2,3-difluoro-4-n-octyloxyphenyl)-5-n-nonyloxypyrimidine is recrystallized from ethanol.

2-(2,3-difluoro-4-n-heptylphenyl)-5-n-nonyloxypyrimidine is obtained analogously by the same reaction sequence from 2,3-difluoro-4-n-heptylbenzamidine.

EXAMPLE 13

0.1 mol of 2-(2,3-difluoro-4-nonylphenyl)-5-hydroxypyridine (prepared by reacting 2,3-difluoro-4-nonylacetophenone successively with benzyloxytrimethinium perchlorate and ammonium acetate with subsequent hydrogenolysis of the benzyl ether) is etherified using 0.11 mol of 1-bromoheptane and 0.11 mol of potassium carbonate in dimethylformamide as solvent. After work-up, the 2-(2,3-difluoro-4-nonylphenyl)-5-heptyloxypyridine is recrystallized from isopropanol.

Analogously, reaction of 2,3-difluoro-4-benzyloxyacetophenone with 2-octyloxytrimethinium perchlorate, ammonium acetate and hydrogenolysis of the benzyl ether gives 2-(2,3-difluoro-4-hydroxyphenyl)-5-octyloxypyridine, which is alkylated using 1-bromodecane to give 2-(2,3-difluoro-4-n-decyloxyphenyl)-5-octyloxypyridine.

The examples below relate to liquid-crystalline phases according to the invention:

EXAMPLE A

A liquid-crystalline phase comprising
8% of 2-p-octyloxyphenyl-5-octylpyrimidine,
12% of 2-p-nonyloxyphenyl-5-octylpyrimidine,
7% of 2-p-hexyloxyphenyl-5-nonylpyrimidine,
23% of 2-p-nonyloxyphenyl-5-nonylpyrimidine,
8% of 2-(2,3-difluoro-4-octyloxyphenyl)-5-nonyl-1,3,4-thiadiazole
8% of 2-(2,3-difluoro-4-octyloxyphenyl)-5-heptyl-1,3,4-thiadiazole
7% of 2-(p-pentyloxyphenyl)-5-(p-heptylphenyl)-1,3,4-thiadiazole,
7% of 2-(p-heptyloxyphenyl)-5-(p-heptylphenyl)-1,3,4-thiadiazole,
6% of 2-(p-heptyloxyphenyl)-5-(2,3-difluoro-4-heptylphenyl)-1,3,4-thiadiazole,
4% of 2-(4,-heptyloxy-2,3-difluorobiphenyl-4-yl)-5-pentyl-1,3,4-thiadiazole and
10% of optically active 4,-octyloxybiphenyl-4-yl 2-cyano-2-methylhexanoate exhibits S$_c$* 66 S$_A$ 70 Ch 80 I and a spontaneous polarization at room temperature of 21 nC/cm².

EXAMPLE B

A liquid-crystalline phase comprising
3% of 2-p-heptyloxyphenyl-5-heptylpyrimidine,
4% of 2-p-nonyloxyphenyl-5-heptylpyrimidine,
11% of 2-p-octyloxyphenyl-5-nonylpyrimidine,
21% of 2-p-nonyloxyphenyl-5-nonylpyrimidine,
7% of 2-(2,3-difluoro-4-octyloxyphenyl)-5-octylpyrimidine,
8% of 2-(2,3-difluoro-4-nonyloxyphenyl)-5-nonylpyrimidine,
4% of 2-(2,3-difluoro-4-octyloxyphenyl)-5-octylpyridine,
7% of 2-(p-heptyloxyphenyl)-5-(p-pentylphenyl)-1,3,4-thiadiazole,
17% of r-1-cyano-cis-4-(4,-octyloxybiphenyl-4-yl)-1-octylcyclohexane,
8% of 2-(4,-pentyloxy-2,3-difluorobiphenyl-4-yl)-5-heptylpyrimidine and
10% of optically active p-(5-heptylpyrimidin-2-yl)-phenyl 2-chloro-3-methylbutyrate
exhibits S$_c$* 2 S$_A$ 66 Ch 78 I and a spontaneous polarization at room temperature of 14 nC/cm².

EXAMPLE C

A liquid-crystalline phase comprising
7% of 2-p-cyanophenyl-5-pentylpyrimidine,
8% of 2-p-cyanophenyl-5-heptylpyrimidine,
8% of 2-p-cyanophenyl-5-(p-butylphenyl)-pyrimidine,
5% of 4-ethyl-4,-(trans-4-propylcyclohexyl)biphenyl,
5% of 4-ethyl-4,-(trans-4-pentylcyclohexyl)biphenyl,
7% of 2-p-methoxyphenyl-5-hexylpyrimidine,
6% of 2-p-nonyloxyphenyl-5-heptylpyrimidine,
7% of 2-p-methoxyphenol-5-nonylpyrimidine,
6% of 2-(2,3-difluoro-4-hexyloxyphenyl)-5-nonylpyridine,
6% of 2-(2,3-difluoro-4-nonyloxyphenyl)-5-nonylpyrimidine,
7% of p-methox-yphenyl trans-4-propylcyclohexanecarboxylate,
7% of p-ethoxyphenyl trans-4-propylcyclohexanecarboxylate
7% of p-methox-yphenyl trans-4-butylcyclohexanecarboxylate
7% of p-ethoxyphenyl trans-4-butylcyclohexanecarboxylate and
7% of p-methoxyphenyl trans-4-pentylcyclohexanecarboxylate
is a nematic mixture having high birefringence and favourable high-mux properties.

We claim:
1. A heterocyclic 1,2-difluorobenzene derivative of the formula I2

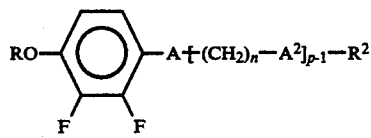

in which R is a straight chain alkyl group having 1 to 15 C atoms in which, in addition, one or more CH₂ may be replaced by a divalent radical selected from —O—, —S—, —CO—, —O—CO—, —CO—O—, —CH=

CH— or —C≡C—, where two heteroatoms are not linked directly to one another, P is 1 or 2, n is 0 or 2, $R^2$ is a straight chain alkyl group having 1–15 C atoms in which, in addition, one or more $CH_2$ groups may be replaced by a divalent radical selected from —O—, —S—, —CO—, —O—CO—, —CO—O, or —C≡C—, where two heteroatoms are not linked directly to one another, $A^2$ is a 1,4-phenylene group which is unsubstituted or monosubstituted or polysubstituted by fluorine, or a trans-1,4-cyclohexylene group, and A is a 1,3,4-thiadiazole-2,5-diyl- or pyridine 2,5-diyl.

2. A difluorobenzene derivative of claim 1, wherein RO is a straight-chain group which is selected from methoxy, ethoxy, butoxy, pentoxy, hexoxy, heptoxy, octoxy, nonoxy, decoxy, undecoxy, dodecoxy, tridecosy, tetradecoxy, 1,3-, 1,4- or 1,5-dioxahexyl and 1,3-, 1,4-, 1,5- or 1,6-dioxaheptyl.

3. A difluorobenzene derivative of claim 1, wherein $R^2$ is a straight-chain alkyl, alkoxy, oxaalkyl or dioxyalkyl group each of 2–12 C atoms.

4. A difluorobenzene derivative of claim 1, wherein n is 0.

5. A difluorobenzene derivative of claim 6, of the formulae having the

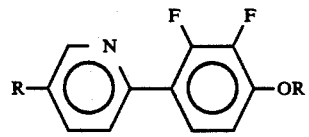

C

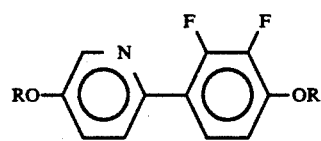

G wherein R is, in each case independently of one another, straight-chain or monobranched alkyl having 3 to 12 C atoms in which, in addition, one $CH_2$ group which is not linked to 0 may be replaced by —O— or —CH=CH—.

6. A difluorobenzene derivative of claim 5, wherein R is alkyl, oxaalkyl or alkenyl having 3 to 12 C atoms.

7. A difluorobenzene derivative of claim 1, wherein A is

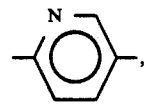

,

8. A liquid-crystalline phase having at least two liquid-crystalline components, which contains at least one compound of the formula I2 according to claim 1.

9. An electrooptical display element, which contains, as dielectric, a phase according to claim 8.

* * * * *